United States Patent
Kim et al.

(10) Patent No.: US 7,975,996 B2
(45) Date of Patent: Jul. 12, 2011

(54) SCAN STAGE FOR SEMICONDUCTOR WAFER POLLUTANT MEASUREMENT APPARATUS

(75) Inventors: Ho Jin Kim, Icheon-si (KR); Hyoung Bae Kim, Seongnam-si (KR)

(73) Assignee: Korea Techno Co., Ltd, Gwangju Si, Gyeonggi-Do (KR)

( * ) Notice: Subject to any disclaimer, the term of this patent is extended or adjusted under 35 U.S.C. 154(b) by 523 days.

(21) Appl. No.: 12/206,152

(22) Filed: Sep. 8, 2008

(65) Prior Publication Data
US 2009/0250569 A1    Oct. 8, 2009

(30) Foreign Application Priority Data

Apr. 3, 2008   (KR) .................. 10-2008-0031130

(51) Int. Cl.
    *B25B 11/00*    (2006.01)

(52) U.S. Cl. .............. 269/21; 269/20; 269/43; 248/363; 248/176.2

(58) Field of Classification Search ............ 269/21, 269/20, 71, 75, 43; 248/363, 362, 176.2
See application file for complete search history.

(56) References Cited

U.S. PATENT DOCUMENTS

| | | | |
|---|---|---|---|
| 3,448,510 A * | 6/1969 | Johnson, Jr. et al. | 29/413 |
| 3,787,039 A * | 1/1974 | Zeichman | 269/13 |
| 4,320,580 A * | 3/1982 | Williams | 33/638 |
| 5,028,182 A * | 7/1991 | Park | 409/225 |
| 5,065,495 A * | 11/1991 | Narushima et al. | 29/559 |
| 5,590,870 A * | 1/1997 | Goellner | 269/21 |
| 5,772,170 A * | 6/1998 | Tsukushi | 248/363 |
| 6,960,265 B2 | 11/2005 | Heo et al. | |
| 2004/0131783 A1 | 7/2004 | Lee | |
| 2009/0250569 A1 * | 10/2009 | Kim et al. | 248/176.1 |

* cited by examiner

*Primary Examiner* — Lee D Wilson
(74) *Attorney, Agent, or Firm* — Lexyoume IP Group, PLLC.

(57) ABSTRACT

Provided is a scan stage for a semiconductor wafer pollutant measurement apparatus, which includes: a stage main body which comprises: a circular fixed housing; an adsorption plate which is rotatably installed in the inside of the fixed housing, at the center of which an adsorption path is formed, at the bottom of which a vacuum port is connected, and which is rotated by an external rotating force; and a step motor which is placed at the bottom of the fixed housing and connected with the adsorption plate; a base plate that is supported by pillars to form a lower space between the fixed housing of the stage main body and the base plate; a cylinder at the bottom of which a cylinder load is connected so that the base plate moves up and down; and support jigs that hold up a wafer in the outer side of the stage main body, in which three support jigs are disposed in proximity with the outer circumference of the stage main body.

8 Claims, 10 Drawing Sheets

SCAN STAGE FOR SEMICONDUCTOR WAFER POLLUTANT MEASUREMENT APPARATUS

CROSS-REFERENCE TO RELATED APPLICATION

This application claims the benefit of Korean Patent Application No. 10-2008-0031130, filed on Apr. 3, 2008, in the Korean Intellectual Property Office, the disclosure of which is incorporated herein by reference.

BACKGROUND OF THE INVENTION

1. Field of the Invention

The present invention relates to a semiconductor wafer pollutant measurement apparatus which is called an auto scanning system, in which the pollutant includes metal impurities, and more particularly, to a scan stage on which a wafer is loaded to then rotate in the case of scanning surface of the wafer in order to collect pollutants such as metal impurities.

2. Description of the Related Art

In general, as a semiconductor device is high-integrated, various kinds of pollutants that are produced in semiconductor manufacturing lines and semiconductor manufacturing processes are adsorbed on the surfaces of wafers. As a result, various kinds of pollutants that are adsorbed on the surfaces of wafers affect performance and yield of semiconductor devices.

Accordingly, an analysis of pollutants having sticked on the wafer surface has become important in manufacturing semiconductor devices. In the case of a conventional pollutant analysis method, a predetermined wafer is selected between the respective semiconductor manufacturing lines or the respective semiconductor manufacturing processes, and the surface of the selected wafer is scanned, to thus collect a sample of pollutants for analyzing the pollutants having sticked on the wafer surface, and analyze the collected pollutants sample using a destructive analysis method such as an atomic absorption spectroscopy and an inductively coupled plasma ICP-mass spectroscopy, and a nondestructive analysis method such as a total X-ray fluorescent analyzer.

That is, according to the conventional art, after the predetermined wafer has been selected between the respective semiconductor manufacturing lines or the respective semiconductor manufacturing processes, an oxide film that has been coated on the wafer surface should be removed before pollutants having sticked on the wafer surface are collected, in order to collect the pollutants accurately. This has been realized by a vapor phase decomposition (VPD) device.

The VPD device includes a process chamber in which a process proceeds, a loading plate which is positioned in the chamber and on which a wafer is loaded, and a container containing a hydrofluoric acid (HF) which decomposes an oxide film that is coated on the wafer surface. If a wafer is transferred on the loading plate which is installed in the process chamber, the wafer is safely placed in the process chamber for a given time. As a result, the oxide film that has been coated on the wafer surface is completely decomposed by vapor of the hydrofluoric acid (HF) which has been naturally evaporated from the hydrofluoric acid (HF) container.

Thereafter, a user takes out the wafer from the process chamber, and then drops a scanning solution on the wafer surface. The user scans the wafer surface directly manually, with the scanning solution, to thereby collect a sample of pollutants for pollution analysis of analyzing the pollutants having sticked on the wafer surface. Of course, the collected sample is analyzed to thereby measure a pollution level.

The Korean Patent Registration No. 10-0383264 entitled "Apparatus and method for collecting metallic impurity on a semiconductor wafer" corresponding to U.S. Patent Application Publication No. US 2002/0134406 A1 is already known as the semiconductor wafer pollutant measurement apparatus. The semiconductor wafer metallic impurity collecting apparatus generally includes a process chamber, a transfer unit, a loader unit, a vapor phase decomposition unit, a scanning unit, a drying unit, an unloader unit, and a center control unit that controls the semiconductor wafer metallic impurity collecting apparatus on the whole.

Here, the transfer unit, the loader unit, the vapor phase decomposition (VPD) unit, the scanning unit, the drying unit, and the unloader unit among the components of the semiconductor wafer metallic impurity collecting apparatus are implemented in the process chamber. That is, the transfer unit, the loader unit, the vapor phase decomposition unit, the scanning unit, the drying unit, and the unloader unit are placed in a semi-circular form where the transfer unit is placed at the center of the semi-circular form, and the loader unit and the unloader unit are placed at the start and end portion of the semi-circular form, respectively. Here, the vapor phase decomposition unit, the scanning unit, and the drying unit are sequentially installed between the loader unit and the unloader unit.

Among the accompanying drawings, FIG. 1 is a partially cutoff perspective view schematically showing the whole structure of a conventional semiconductor wafer pollutant measurement apparatus.

As illustrated in FIG. 1, if a predetermined wafer is selected to analyze a pollution level of the selected wafer at a semiconductor manufacturing line or process, a user transfers the selected wafer to a loader unit which is positioned in the process chamber of the semiconductor wafer pollutant measurement apparatus.

Thereafter, if the user tightly closes the process chamber and then makes the semiconductor wafer pollutant measurement apparatus operate, the transfer unit transfers the wafer located in the loader unit to the loading plate in the vapor phase decomposition (VPD) unit. Then, the vapor phase decomposition (VPD) unit tightly seals the wafer transferred to the loading plate and then decomposes an oxide film coated on the wafer surface using vapor of the hydrofluoric acid (HF).

Then, if the oxide film coated on the wafer surface has been completely decomposed, the transfer unit transfers the wafer located in the vapor phase decomposition (VPD) unit again to an align unit in the scanning device.

Thereafter, the wafer align unit aligns position of the transferred wafer accurately using an align hand, and simultaneously the scanning arm is rotated into the position of a nozzle tray. Accordingly, the nozzle provided in the nozzle tray is inserted into the scanning arm. Then, the scanning arm makes the nozzle inhale a predetermined amount of a scan solution from a scan solution bottle which is installed at the center of the nozzle tray, and then moves to the upper portion of the wafer, to thereafter approach the center of the wafer slowly.

Then, the scanning arm stops the approach when the center of the wafer substantially contacts the nozzle inserted into the scanning arm. If the approach of the scanning arm to the center of the wafer stops, a pump discharges part of the scan solution inhaled by the nozzle via a pumping fluid path of the scanning arm to the surface of the wafer, and makes the scan solution cohered in a droplet form between the lower portion of the nozzle and the wafer surface.

Thereafter, if the scan solution is cohered in a droplet form in the lower portion of the nozzle that has been inserted into the scanning arm and contacts the wafer surface, the wafer align unit makes the wafer rotate in one direction slowly, and the scanning arm makes the lower portion of the nozzle, that is, a portion where the scan solution contacts the wafer surface move slowly in one direction. Here, as the pollutants on the wafer surface contacts the externally exposed scan solution, they are of course absorbed into the scan solution.

Here, when the scanning arm moves once, a wafer takes a turn, and when the scanning arm moves once again, the wafer takes a turn again. That is, the wafer is scanned in a step-by-step style. As described above, if the scan solution is not seceded from the lower portion of the nozzle but scanning of a wafer is ended, the wafer align unit stops rotation and the scanning arm also stops movement. In this case, the pump inhales all the scan solution which has been used for scanning the wafer into the nozzle using the pumping fluid path.

Thereafter, the scanning arm operates by two methods according to user's selection.

One hand, in the case that a user wishes to analyze a wafer using an atomic absorption spectroscopy, the scanning arm rotates to move toward a sampling cup tray so that all the pollutant samples which have been used for scanning the wafer are discharged into a sampling cup. If the pollutant samples which have been used for scanning the wafer have been completely discharged into the sampling cup, the scanning arm rotates again so that the nozzle is positioned at the upper portion of the nozzle bottle. Then, the nozzle which has been inserted into the scanning arm is seceded from the scanning arm using a nozzle secession unit which is installed in the scanning device, so as to be distant from the nozzle bottle.

Thereafter, the wafer is transferred to the unloader unit by the transfer unit, and simultaneously unloaded to the outside. As a result, the pollutants collection process is ended.

On the other hand, in the case that a user wishes to analyze a wafer by a total reflection fluorescence X-ray analysis, the scanning arm discharges the pollutant samples which have been used for scanning the wafer to the center of the wafer surface slowly again, and rotates again to make the nozzle positioned at the upper portion of the nozzle bottle. Then, the nozzle which has been inserted into the scanning arm is seceded from the scanning arm using a nozzle secession unit which is installed in the scanning arm so as to be distant from the nozzle bottle. Then, the wafer is transferred to a heating plate in a drying unit, and then dried, to then be transferred to the unloader unit. As a result, the pollutants collection process is ended.

A conventional scan stage which has been known as being used in a process of scanning and collecting pollutants for a semiconductor wafer pollutant measurement apparatus maintains nothing but a loaded state of a wafer, and has only a structure of making both side surfaces of a rotating plate contact a rotating roller to then rotate. Further, whenever a wafer is made to move, an end effector of a robot arm is inserted for itself into the bottom of the wafer so that the wafer is loaded, to thus cause an unstable factor.

SUMMARY OF THE INVENTION

To overcome inconveniences of the conventional scan stage for a semiconductor wafer pollutant measurement apparatus, it is an object of the present invention to provide a scan stage for a semiconductor wafer pollutant measurement apparatus, which makes a wafer persistently adsorbed on a rotating plate under the control of inhalation and discharging of a vacuum pressure.

It is another object of the present invention to provide a scan stage for a semiconductor wafer pollutant measurement apparatus, which enables a base plate located at the lower portion of the scan stage to move up and down and thus makes it easy to do effecting of the lower portion of a wafer when the wafer is loaded.

It is still another object of the present invention to provide a scan stage for a semiconductor wafer pollutant measurement apparatus, which makes a wafer adsorption plate in the scan stage rotate.

It is yet another object of the present invention to provide a scan stage for a semiconductor wafer pollutant measurement apparatus, which includes independent jigs which may be easily separated when a wafer is loaded at the outer side of the scan stage.

It is a further object of the present invention to provide a scan stage for a semiconductor wafer pollutant measurement apparatus, which includes a device for detecting whether or not a wafer is loaded or whether or not a rotating body rotates.

It is a still further object of the present invention to provide a scan stage for a semiconductor wafer pollutant measurement apparatus, in which structure of an adsorption plate is improved to be rotatable in the inside of a fixed housing and an adsorbing unit is formed on the upper surface of a rotating body so that a wafer is adsorbed under the vacuum condition and the wafer is persistently adsorbed on the scan stage as a vacuum line and a vacuum port.

It is a yet further object of the present invention to provide a scan stage for a semiconductor wafer pollutant measurement apparatus, which is divided into a rotating body and a fixed housing in which a step motor is installed in the fixed housing to thus precisely control stepwise rotation of the rotating body.

It is a yet still further object of the present invention to provide a scan stage for a semiconductor wafer pollutant measurement apparatus, which includes a jig which can chuck both 12-inch and 8-inch wafers.

To accomplish the above object of the present invention, according to an aspect of the present invention, there is provided a scan stage for a semiconductor wafer pollutant measurement apparatus, the scan stage comprising:

a stage main body which comprises: a circular fixed housing; an adsorption plate which is rotatably installed in the inside of the fixed housing, at the center of which an adsorption path is formed, at the bottom of which a vacuum port is connected, and which is rotated by an external rotating force; and a step motor which is placed at the bottom of the fixed housing and connected with the adsorption plate;

a base plate that is supported by pillars to form a lower space between the fixed housing of the stage main body and the base plate;

a cylinder which is connected with a cylinder load which is formed at the bottom of the base plate so that the base plate moves up and down; and support jigs that hold up wafers in the outer side of the stage main body, respectively.

Preferably but not necessarily, the adsorption plate further comprises a rotating body which is driven by a step motor which is placed at the outer side of the adsorption plate.

Preferably but not necessarily, each jig comprises a first support step portion and a second support step portion which support 12-inch and 8-inch wafers, respectively.

Preferably but not necessarily, each jig further comprises sensors which detect whether or not a wafer is loaded.

Preferably but not necessarily, the adsorption plate is rotatably installed in the inside of the fixed housing and an adsorbing unit is formed on the upper surface of the rotating body and a vacuum line is formed in the inside of the rotating body so as to be connected with a vacuum port which is placed at the bottom of the rotating body.

BRIEF DESCRIPTION OF THE DRAWINGS

The above and/or other aspects of the present invention will become apparent and more readily appreciated from the following description of the exemplary embodiments, taken in conjunction with the accompanying drawings in which.

DETAILED DESCRIPTION OF THE INVENTION

Figure 1:
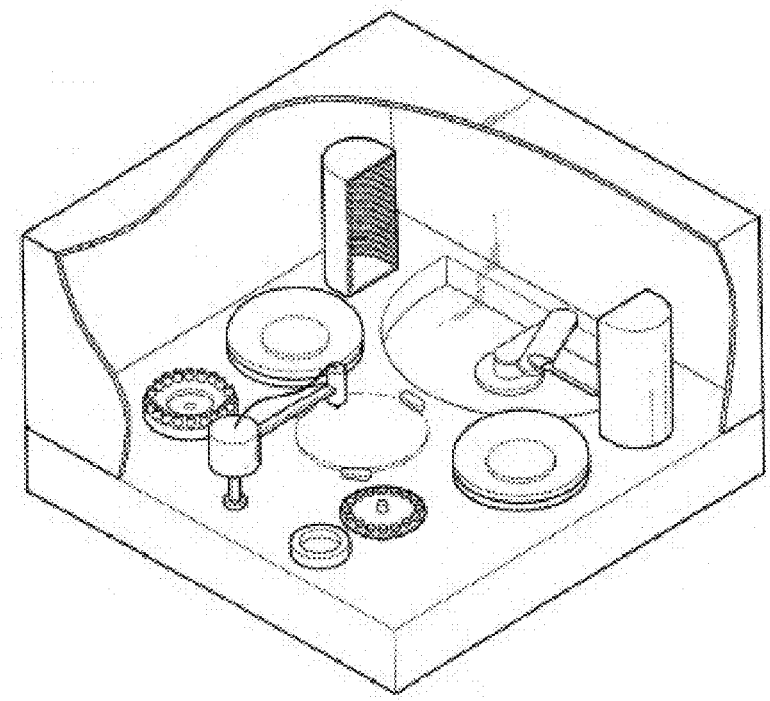
FIG. 1 is a perspective view showing the inside of a conventional semiconductor wafer pollutant measurement apparatus.

Hereinbelow, a scan stage for a semiconductor wafer pollutant measurement apparatus which is called an auto scanning system, according to an embodiment of the present invention will be described with reference to the accompanying drawings. Like reference numerals are assigned for like elements in the drawings.

Figure 2A:
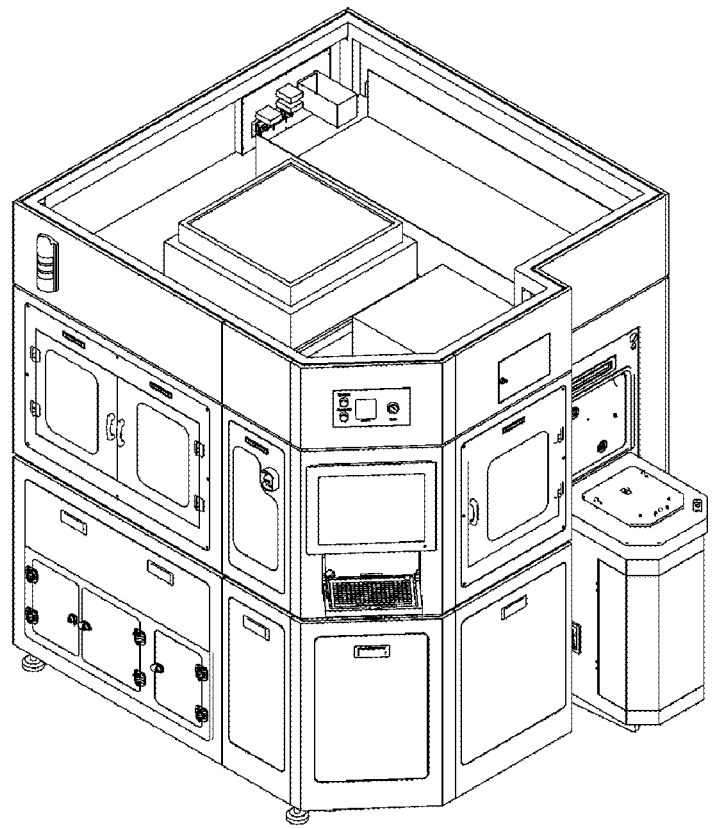
FIG. 2A is a perspective view showing the whole external appearance of a semiconductor wafer pollutant measurement apparatus, according to an embodiment of the present invention.
Figure 2B:
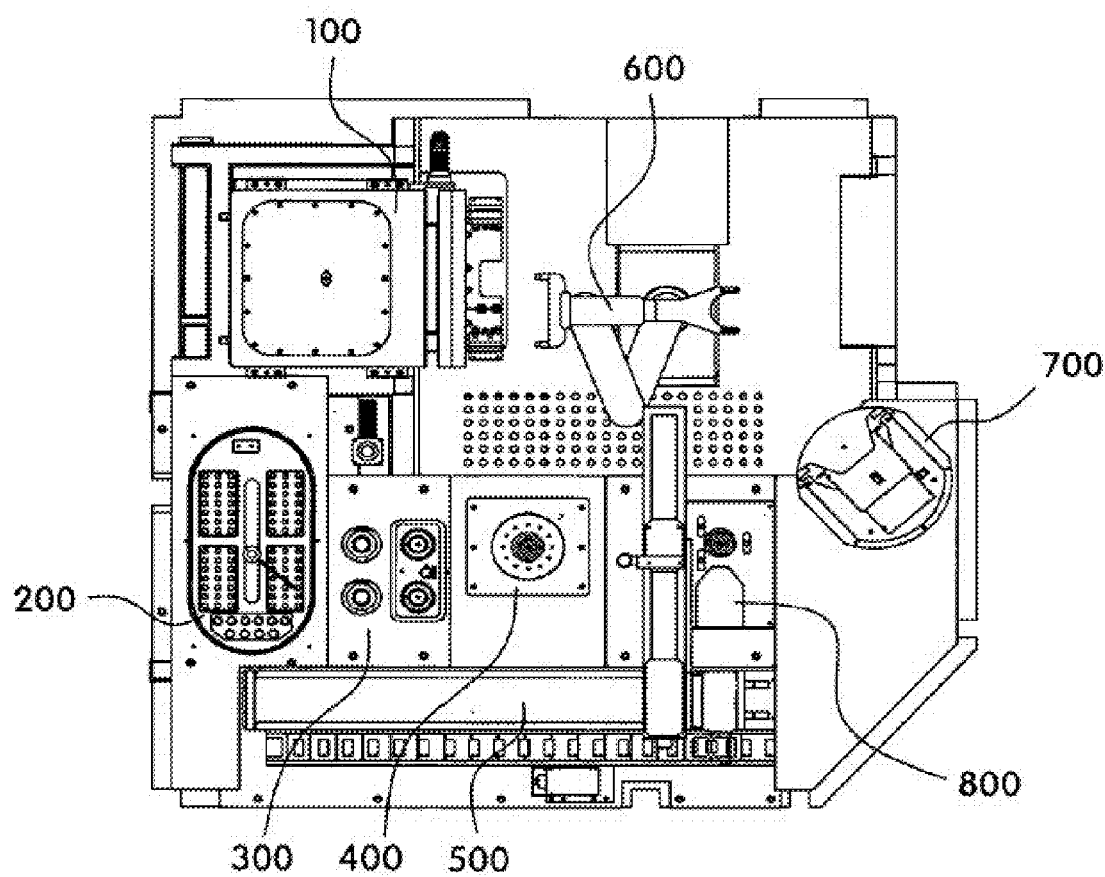
FIG. 2B is a schematic plan view showing the inside of the semiconductor wafer pollutant measurement apparatus of FIG. 2A.

FIG. 2A is a perspective view showing the whole external appearance of a semiconductor wafer pollutant measurement apparatus according to the present invention, and FIG. 2B is a schematic plan view showing the inside of the semiconductor wafer pollutant measurement apparatus of FIG. 2A.

As shown in FIGS. 2A and 2B, a semiconductor wafer pollutant measurement apparatus according to the present invention, includes: an opener 700 which is located at an entrance portion in a space which is isolated from the outside portion, and opens a wafer cassette according to size of a wafer such as 300 mm, 200 mm, and 150 mm, for example; a robot arm 600 that picks up a wafer in a cassette that is safely loaded into the opener 700 and transfers the picked wafer; a vapor phase decomposition (VPD) device 100 which primarily decomposes an oxide film formed on the surface of the wafer that is transferred by the robot arm 600; a scan stage 400 which supports the wafer whose oxide film has been decomposed and rotates the wafer at a state where the wafer has been supported; and a scanning unit 500 according to the present invention which moves along three axes of x, y and z, and inhales a reagent from a reagent solution inhalation and washing unit 300 and then moves to the scan stage 400 to thus perform a scanning operation on the wafer put on the scan stage 400, in order to make the wafer put on the scan stage 400 contact a solution, and to thereafter discharge the scanned solution into a bottle of an analyser unit 200. After having discharged, the inhalation and discharge nozzle of the scanning unit 500 is washed in the reagent solution inhalation and washing unit 300 to then inhale the reagent from the reagent solution inhalation and washing unit 300 and to repeat a scanning operation.

Description of scanning will be omitted. Here, if the scanning unit 500 reaches a predetermined position of a wafer at a state where a predetermined amount of solution is inhaled into the nozzle, it rotates the wafer and discharges part of the solution to contact the surface of the wafer. In this case, if the scanning unit 500 moves along most surfaces of the wafer in a straight line, and simultaneously makes the wafer rotate, it makes most surfaces of the wafer contact the solution so that pollutants can be collected. The solution containing the collected pollutants is transferred to the analyzer unit 200 at a state where the nozzle is in an inhalation position to then be discharged into an empty bottle of the analyzer unit 200.

Thereafter, the transfer unit robot arm 600 transfers the wafers whose tests are finished to an aligner unit 800, to thereby make the aligner unit 800 recognize identification (ID) of each wafer and align the wafers, to then remove the aligned wafers into a cassette.

If the solution having included the pollutants is discharged to the bottle of the analyzer unit 200, the whole operation of this invention ends. Then, a user measures a pollution level in every bottle through a semiconductor wafer pollutant measurement apparatus.

Figure 3:
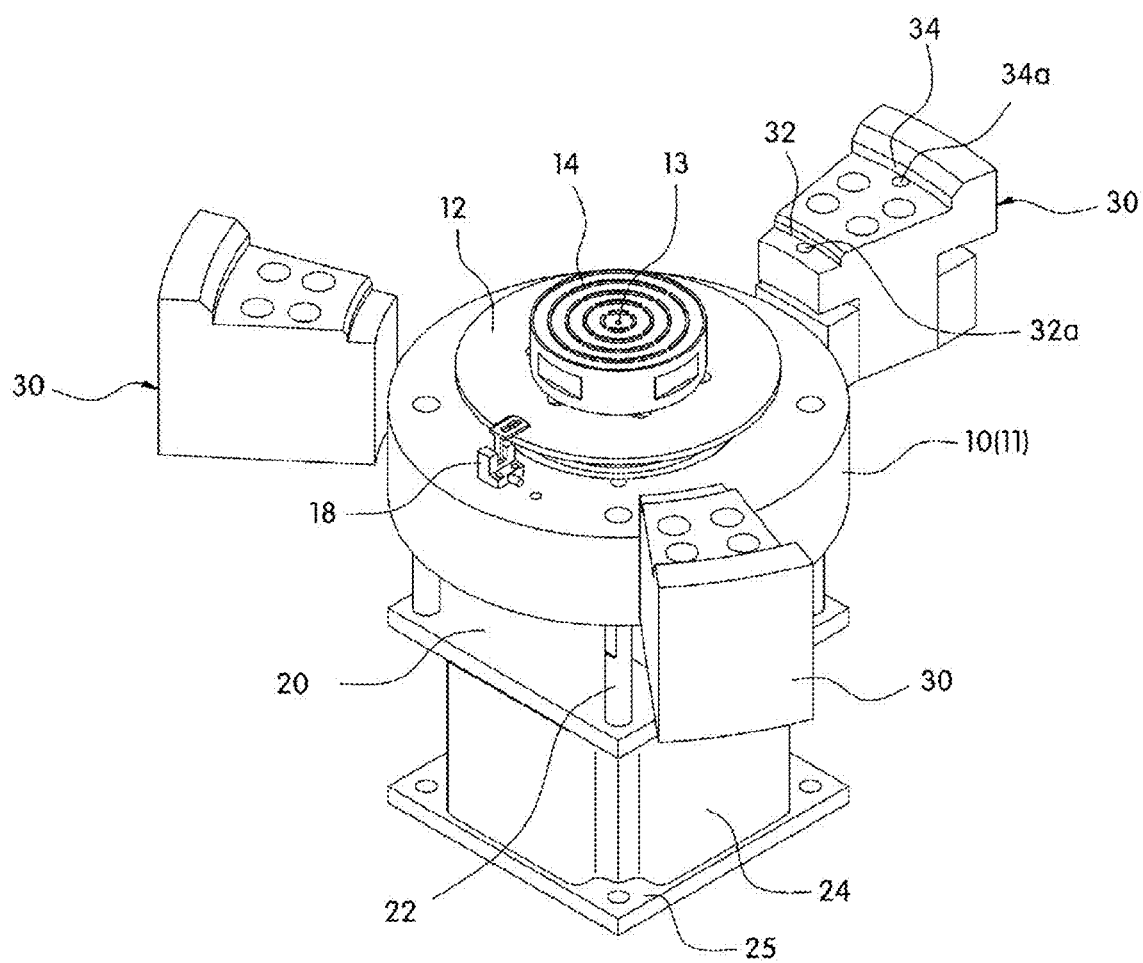
FIG. 3 is an extracted perspective view showing a scan stage for a semiconductor wafer pollutant measurement apparatus according to an embodiment of the present invention.
Figure 4:
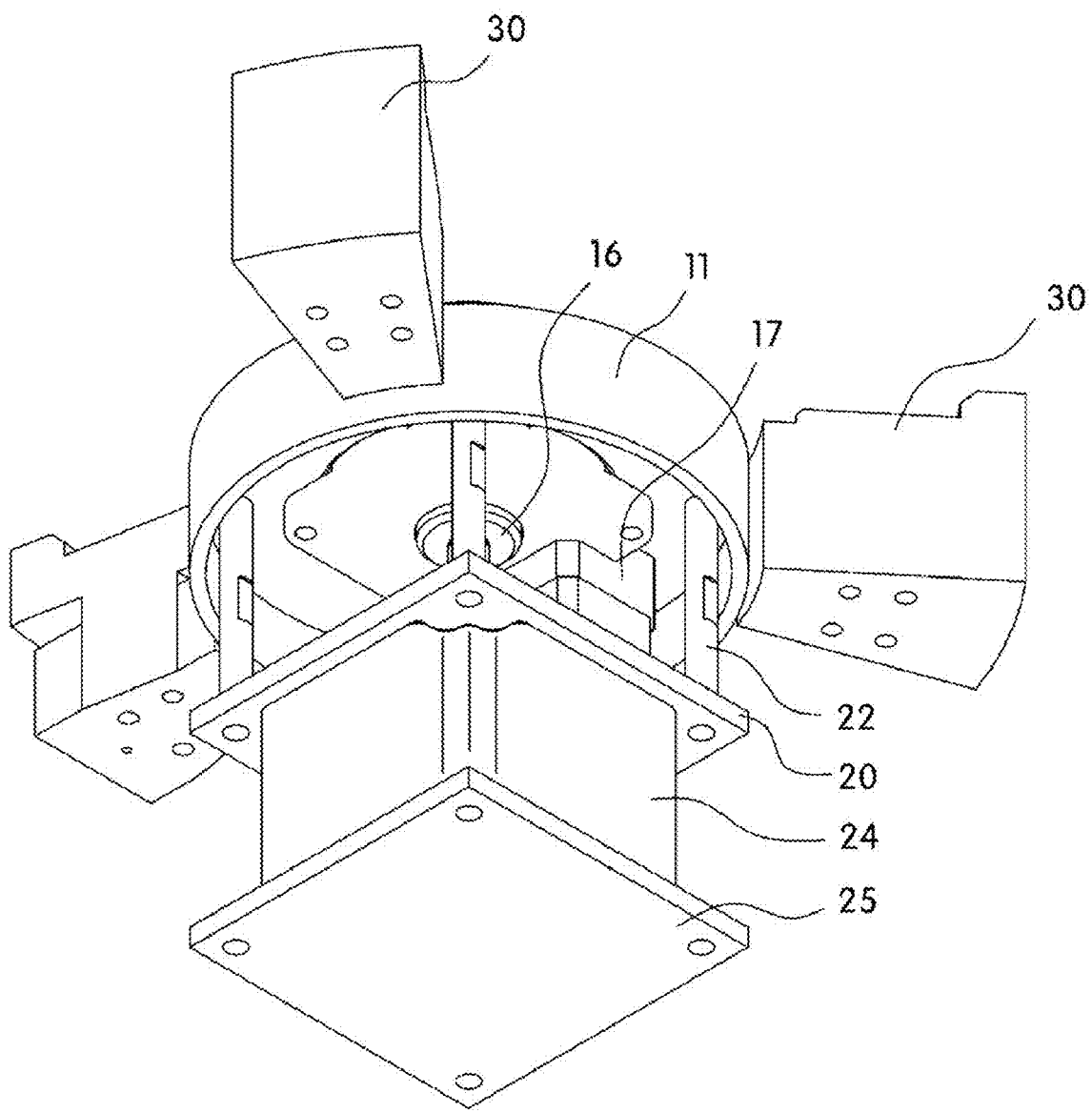
FIG. 4 is an extracted perspective view showing a scan stage for a semiconductor wafer pollutant measurement apparatus, viewed from the bottom, according to an embodiment of the present invention.
Figure 5:
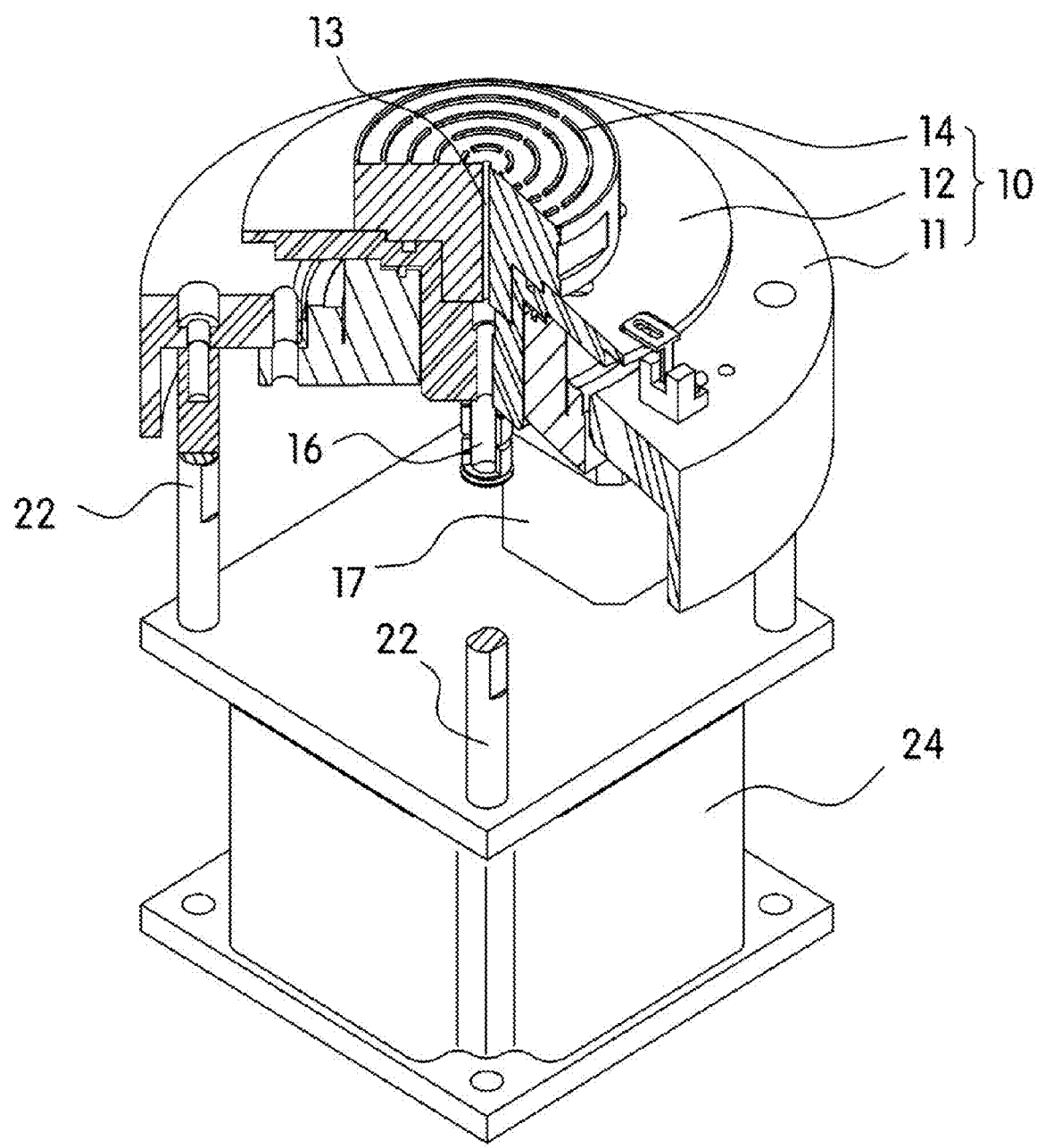
FIG. 5 is a partially cutoff extracted perspective view showing a scan stage for a semiconductor wafer pollutant measurement apparatus according to an embodiment of the present invention.

FIG. 3 is an extracted perspective view showing a scan stage for a semiconductor wafer pollutant measurement apparatus according to an embodiment of the present invention. FIG. 4 is an extracted perspective view showing a scan stage for a semiconductor wafer pollutant measurement apparatus, viewed from the bottom, according to an embodiment of the present invention. FIG. 5 is a partially cutoff extracted perspective view showing a scan stage for a semiconductor wafer pollutant measurement apparatus according to an embodiment of the present invention.

As shown in FIGS. 3 to 5, the scan stage for the semiconductor wafer pollutant measurement apparatus according to an embodiment of the present invention includes a scan stage main body 10, a base plate 20 and support jigs 30.

First, the stage main body 10 includes: a circular fixed housing 11; a rotating body 12 which is rotatably installed in the inside of the fixed housing 11; an adsorption plate which includes an adsorption path which is formed at the center of the rotating body 12 and an adsorption unit 13 which is formed on the upper surface of the rotating body 12, and at the bottom of which a vacuum port is connected; and a step motor 17 which is placed at the bottom of the fixed housing 11 and is rotated in axial engagement with the shaft of the rotating body 12.

Therefore, a wafer that gets close to the adsorption plate 14 through a vacuum port 16 is adsorbed by an adsorption hole 13, under a vacuum condition, and persistently adsorbed on the adsorption plate 14. The rotating body 12 to which the wafer has been adsorbed is driven by the step motor 17 which is placed at the lower portion of the fixed housing 11, to them rotate. As the wafer rotates by rotation of the rotating body 12, the aforenamed scanning work is achieved.

Figure 8A:
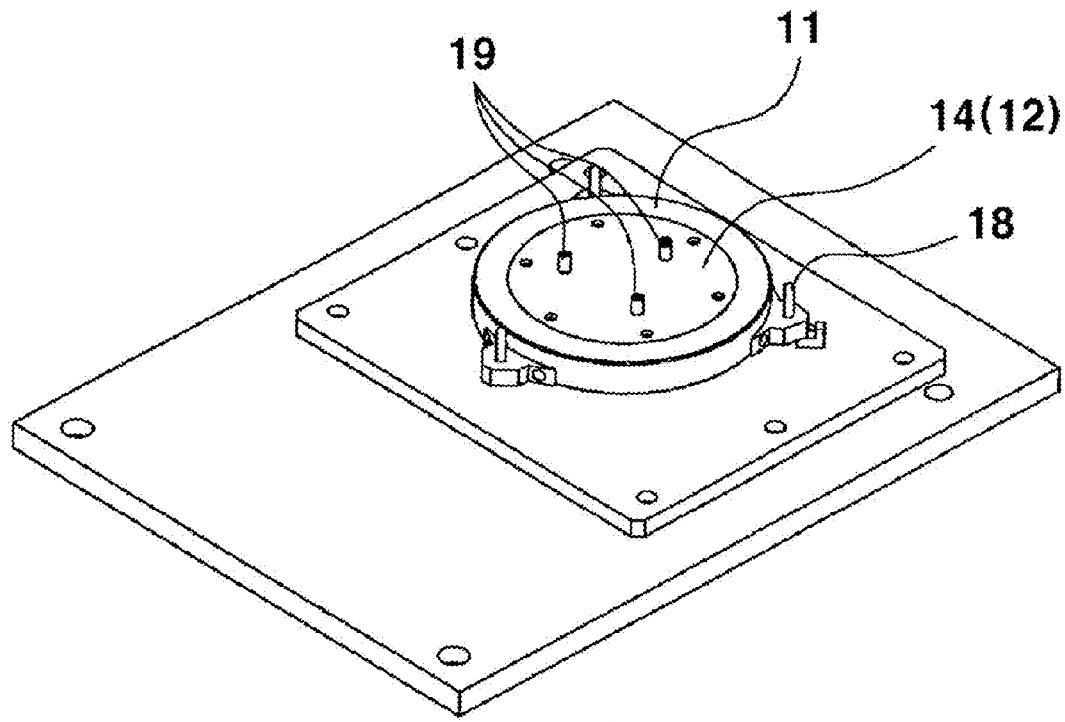
FIGS. 8A, 8B, and 8C are perspective views showing a scan stage for a semiconductor wafer pollutant measurement apparatus according to another embodiment of the present invention, respectively.

Alternatively, the rotating body 12 and the adsorption plate 14 are not separated but may be integrally implemented. In this case, instead of the adsorption hole 13, an adsorption unit 19 of FIG. 8A is formed on the adsorption plate 14, in which the adsorption unit 19, for example, adsorption tubes which communicate with a vacuum line 15 communicating with a vacuum port 16 are protrudingly formed on the upper surface of the adsorption plate 14.

Meanwhile, a sensor 18 which detects whether or not the rotational adsorption plate 14 rotates is formed on the fixed housing 11, to thus detect an initial rotational position of the rotating body 12.

The base plate 20 is supported by pillars 22 to form a lower space between the fixed housing 11 of the stage main body 10 and the base plate 20. A cylinder 24 is connected with a cylinder load 23 (FIG. 6A) which is formed at the bottom of the base plate 20 so that the base plate moves up and down.

The support jigs 30 hold up wafers in the outer side of the stage main body 10, respectively. In the drawings, three support jigs 30 are disposed tri-sectionally at equal angles, nearby around the circumference of the scan stage main body 10. The support jigs 30 are arranged separately from the fixed housing 11, in which both 12-inch and 8-inch wafers may be selectively loaded by the support jigs 30.

Each jig 30 includes a first support step portion 32 and a second support step portion 34 which support 12-inch and 8-inch wafers, respectively.

Each jig 30 further includes sensors 32a and 34a which detect whether or not a 12-inch or 8-inch wafer is loaded, to thereby distinguish a wafer into a 12-inch or 8-inch wafer in size, as well as detection of whether or not a wafer is loaded.

Figure 6A:
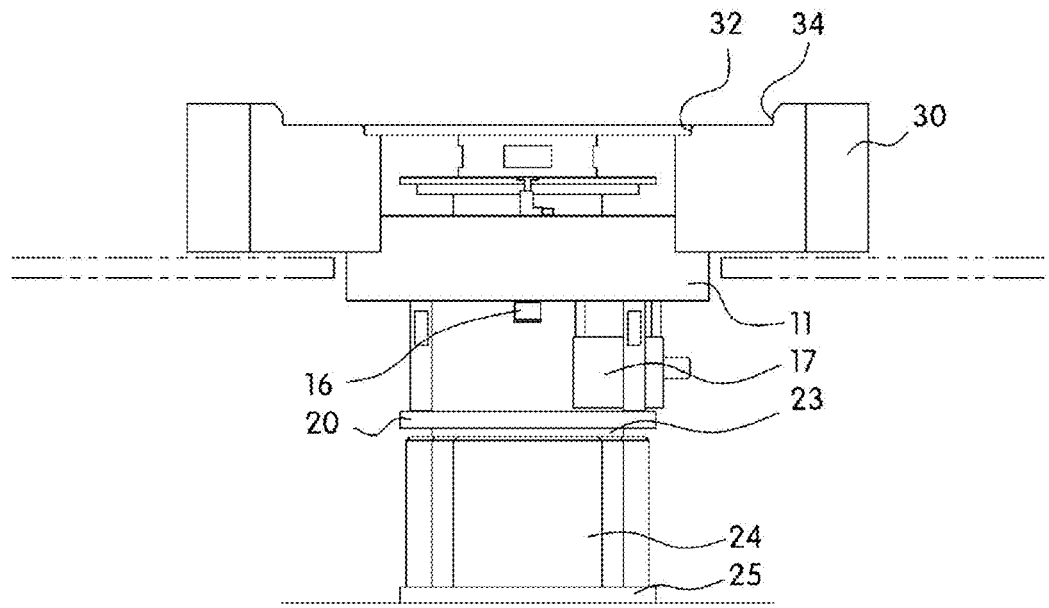
FIGS. 6A and 6B are schematic side views for explaining ascending and descending operations of the scan stage for the semiconductor wafer pollutant measurement apparatus according to an embodiment of the present invention.
Figure 6B:
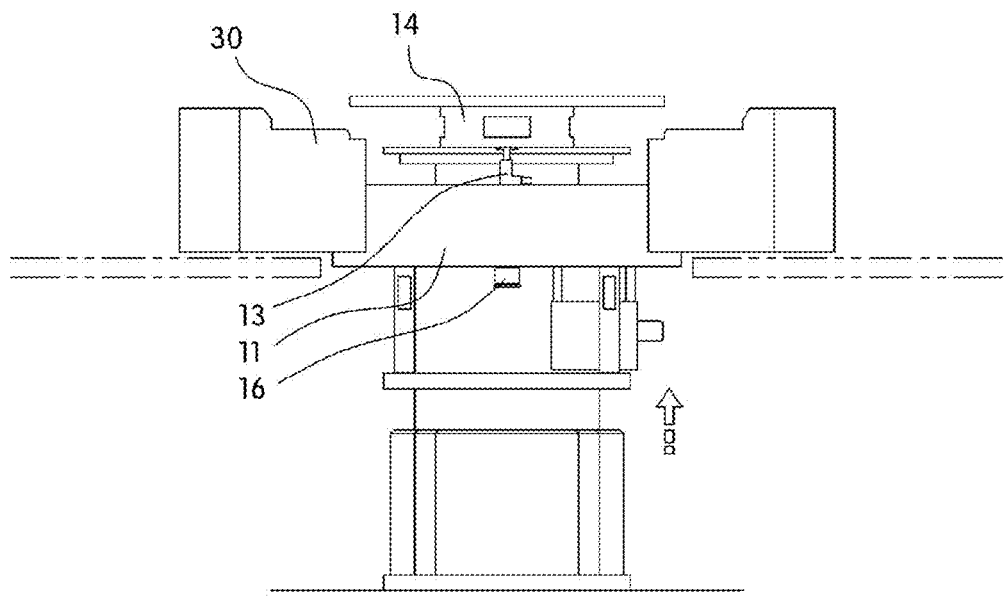

FIGS. 6A and 6B are schematic side views for explaining ascending and descending operations of the scan stage for the semiconductor wafer pollutant measurement apparatus according to an embodiment of the present invention.

The ascending and descending operations of the scan stage for the semiconductor wafer pollutant measurement apparatus according to an embodiment of the present invention, will be described below with reference to FIGS. 6A and 6B.

The cylinder 24 which is located at the lower portion of the base plate 20 is at a descent state (FIG. 6A). Thereafter, if the cylinder 24 is made to operate to push up the cylinder load 23, the base plate 20 which is connected with the upper portion of the cylinder load 23 moves up (FIG. 6B).

The pillars 22 of the base plate 20 hold up the fixed housing 11. Accordingly, as the fixed housing 11 is made to rise up, it is possible to perform an end effecting of a robot arm for a wafer which is loaded in the adsorption plate 14.

Preferably, a gear connection structure is formed between the rotational shaft of the step motor 17 and the rotating body 12 in the lower portion of the fixed housing 11 in order to make the rotating body 12 rotate by rotation of the step motor 17. In this invention, the detailed gear connection structure will be omitted.

When a vacuum state of the vacuum pot 16 is released, wafers loaded on the support jigs 30 move upwards so that the scan arm performs an end effecting operation of the wafers. This is risen up by operation of the cylinder 24. If the wafer rises up to a predetermined height, the robot arm, that is, the scan arm lifts the wafer to thus make the wafer move.

Figure 7A:
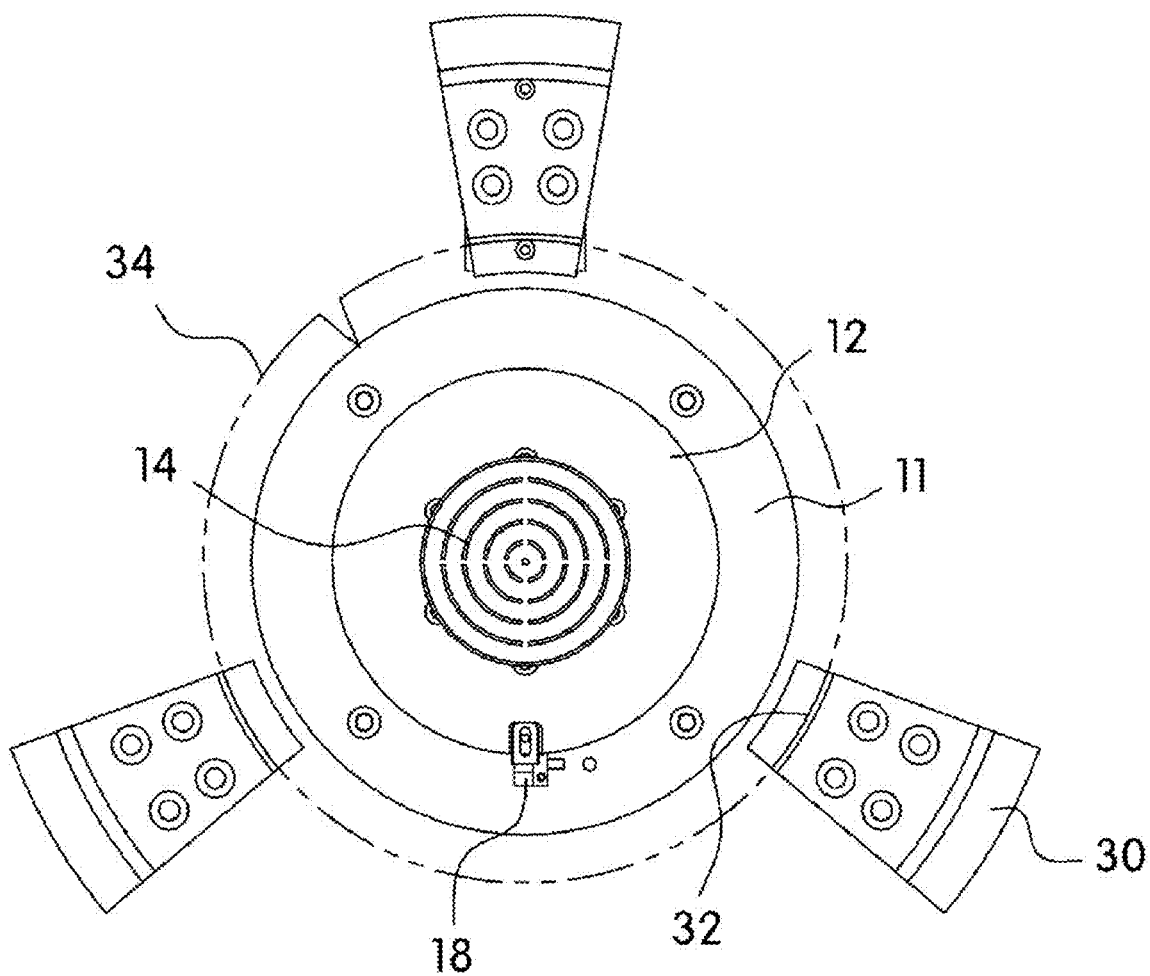
FIGS. 7A and 7B are schematic plan views for explaining that respectively different sized wafers can be selectively loaded in the scan stage for the semiconductor wafer pollutant measurement apparatus according to an embodiment of the present invention.
Figure 7B:
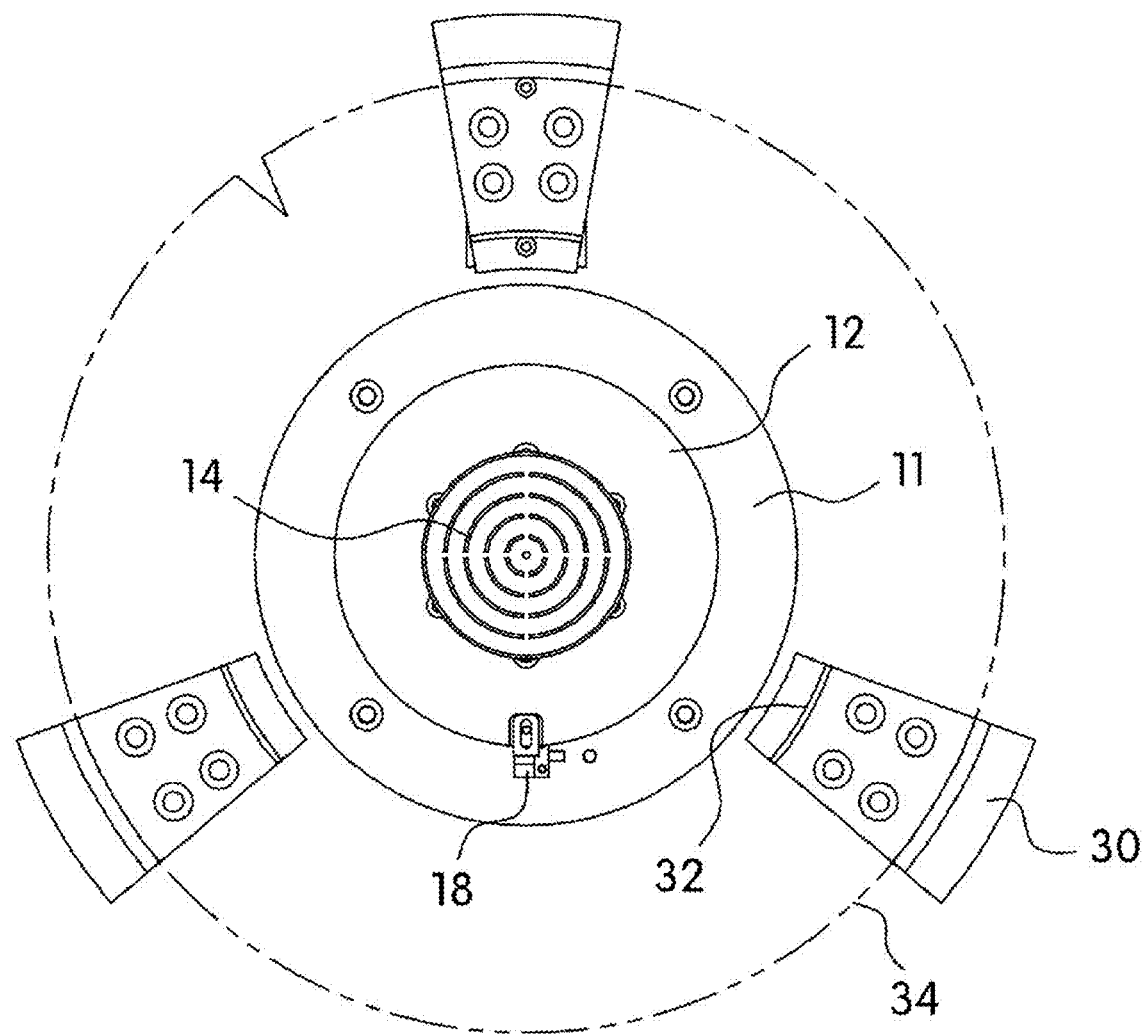

FIGS. 7A and 7B are schematic plan views for explaining that respectively different sized wafers can be selectively loaded in the scan stage for the semiconductor wafer pollutant measurement apparatus according to an embodiment of the present invention.

As shown in FIGS. 7A and 7B, three support jigs 30 of the scan stage according to the present invention are disposed tri-sectionally at equal angles, nearby around the circumference of the scan stage main body 10, so as to support the wafers at the outer side of the scan stage main body 10, respectively. As described above, each jig 30 includes a first support step portion 32 and a second support step portion 34 which support 12-inch and 8-inch wafers, respectively. Each jig 30 further includes sensors 32a and 34a which detect whether or not a 12-inch or 8-inch wafer is loaded, to thereby distinguish a wafer into a 12-inch or 8-inch wafer in size, as well as detection of whether or not a wafer is loaded.

That is, FIG. 7A illustrates a state where a 12-inch wafer is loaded, in which the 12-inch wafer is located at the second support step portion 34 of each jig 30, and FIG. 7B illustrates a state where an 8-inch wafer is loaded, in which the 8-inch wafer is located at the first support step portion 32 of each jig 30.

Figure 8B:
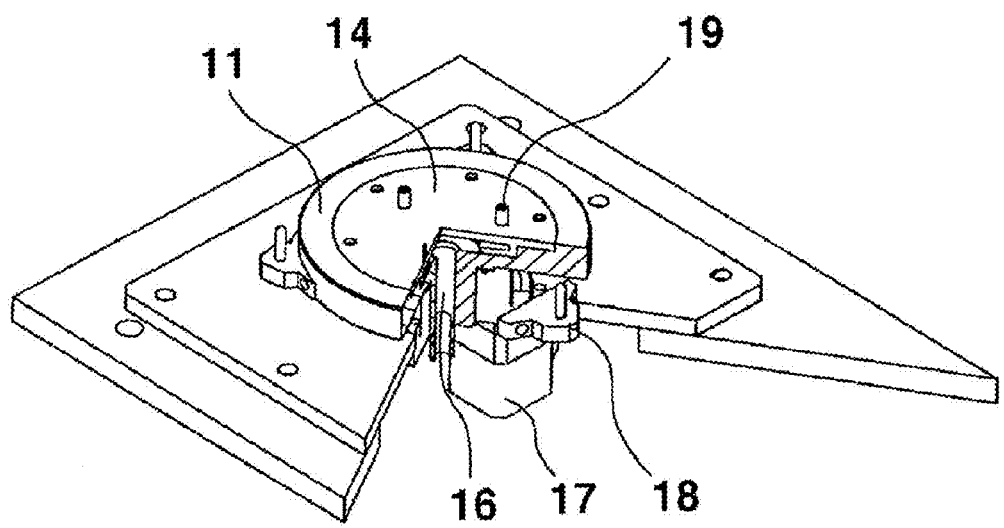
Figure 8C:
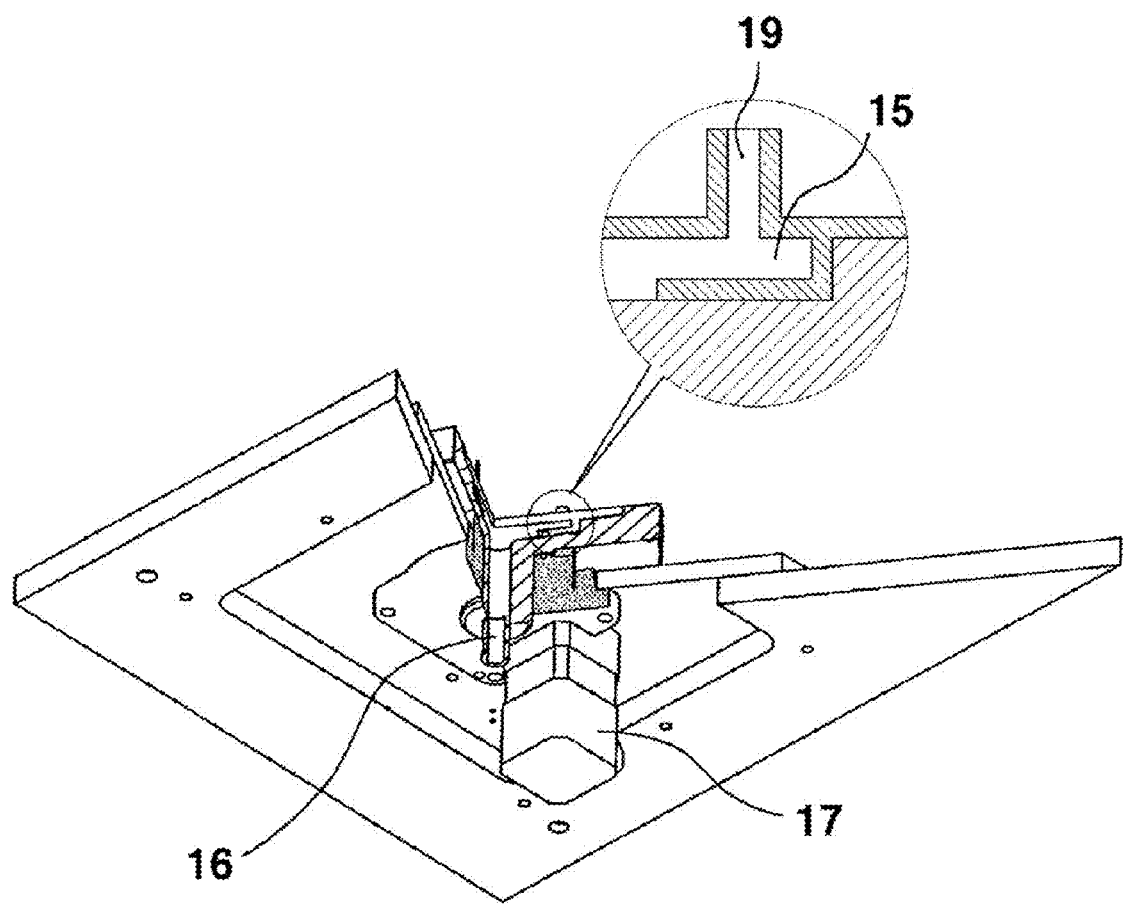

FIGS. 8A, 8B, and 8C are perspective views showing a scan stage for a semiconductor wafer pollutant measurement apparatus according to another embodiment of the present invention, respectively.

In this embodiment, a wafer is also loaded on the adsorption plate 14 in which the wafer is adsorbed through a vacuum port 16 to thus prevent movement of the wafer.

That is, the adsorption plate 14 communicates with a vacuum line 15 which is formed in the inside of the adsorption plate 14 at the vacuum port 16 which is located at the bottom of the adsorption plate 14. A few adsorption tubes 19 are protrudingly formed on the adsorption plate 14, in communication with the vacuum line 15.

The adsorption plate 14 according to the present invention persistently adsorbs wafers through the vacuum port 16 and simultaneously makes the rotating body 12 rotate at a predetermined speed by the step motor 17 which is installed at the lower portion of the fixed housing 11, to thereby perform a scanning work of pollutants.

The present invention is not limited to the above-described embodiments. It is apparent to one who has an ordinary skill in the art that there may be many modifications and variations within the same technical spirit of the invention.

As described above, the present invention has an effect of providing a scan stage for a semiconductor wafer pollutant measurement apparatus, which makes a wafer persistently adsorbed on a rotating plate under the control of inhalation and discharging of a vacuum pressure.

The present invention has an effect of providing a scan stage for a semiconductor wafer pollutant measurement apparatus, which enables a base plate located at the lower portion of the scan stage to move up and down and thus makes it easy to do effecting of the lower portion of a wafer when the wafer is loaded.

The present invention has an effect of providing a scan stage for a semiconductor wafer pollutant measurement apparatus, which makes a wafer adsorption plate in the scan stage rotate, in which a rotating body of the wafer adsorption plate is separated from a fixed body.

The present invention has an effect of providing a scan stage for a semiconductor wafer pollutant measurement apparatus, which includes independent jigs which may be easily separated when a wafer is loaded at the outer side of the scan stage.

The present invention has an effect of providing a scan stage for a semiconductor wafer pollutant measurement apparatus, which includes a device for detecting whether or not a wafer is loaded or whether or not a rotating body rotates.

The present invention has an effect of providing a scan stage for a semiconductor wafer pollutant measurement apparatus, in which structure of an adsorption plate is improved to be rotatable in the inside of a fixed housing and an adsorbing unit is formed on the upper surface of a rotating body so that a wafer is adsorbed under the vacuum condition and the wafer is persistently adsorbed on the scan stage as a vacuum line and a vacuum port.

The present invention has an effect of providing a scan stage for a semiconductor wafer pollutant measurement apparatus, which is divided into a rotating body and a fixed housing in which a step motor is installed in the fixed housing to thus precisely control stepwise rotation of the rotating body.

The present invention has an effect of providing a scan stage for a semiconductor wafer pollutant measurement apparatus, which includes a jig which can chuck both 12-inch and 8-inch wafers.

What is claimed is:

1. A scan stage for a semiconductor wafer pollutant measurement apparatus, the scan stage comprising:
    a stage main body which comprises: a circular fixed housing; an adsorption plate which is rotatably installed in the inside of the fixed housing, at the center of which an adsorption path is formed, at the bottom of which a vacuum port is connected, and which is rotated by an external rotating force; and a step motor which is placed at the bottom of the fixed housing and connected with the adsorption plate;
    a base plate that is supported by pillars to form a lower space between the fixed housing of the stage main body and the base plate;
    a cylinder is connected with a cylinder load which is formed at the bottom of the base plate so that the base plate moves up and down; and
    support jigs that hold up wafers in the outer side of the stage main body, respectively.

2. The scan stage according to claim 1, wherein the adsorption plate further comprises a rotating body which is driven by a step motor which is placed at the outer side of the adsorption plate.

3. The scan stage according to claim 1, wherein each jig comprises a first support step portion and a second support step portion which support 12-inch and 8-inch wafers, respectively.

4. The scan stage according to claim 3, wherein each jig further comprises sensors which detect whether or not a wafer is loaded.

5. The scan stage according to claim 1, wherein the fixed housing further comprises a sensor which detects whether or not the rotating body rotates.

6. The scan stage according to claim 1, wherein the adsorption plate is rotatably installed in the inside of the fixed housing and an adsorbing unit is formed on the upper surface of the rotating body and a vacuum line is formed in the inside of the rotating body so as to be connected with a vacuum port which is placed at the bottom of the rotating body.

7. The scan stage according to claim 2, wherein each jig comprises a first support step portion and a second support step portion which support 12-inch and 8-inch wafers, respectively.

8. The scan stage according to claim 2, wherein the adsorption plate is rotatably installed in the inside of the fixed housing and an adsorbing unit is formed on the upper surface of the rotating body and a vacuum line is formed in the inside of the rotating body so as to be connected with a vacuum port which is placed at the bottom of the rotating body.

* * * * *